United States Patent
Wang et al.

(10) Patent No.: US 6,673,302 B2
(45) Date of Patent: Jan. 6, 2004

(54) WET PROCESSING METHOD FOR CATHETER BALLOONS

(75) Inventors: Lixiao Wang, Long Lake, MN (US); Mona Dahdah, West St. Paul, MN (US); Ron Drake, St. Louis Park, MN (US); Daniel Horn, Shoreview, MN (US)

(73) Assignee: SciMed Life Systems, Inc., Maple Grove, MN (US)

( * ) Notice: Subject to any disclaimer, the term of this patent is extended or adjusted under 35 U.S.C. 154(b) by 390 days.

(21) Appl. No.: 09/768,490

(22) Filed: Jan. 24, 2001

(65) Prior Publication Data

US 2002/0098373 A1 Jul. 25, 2002

(51) Int. Cl.[7] .................. B29C 49/04; B29C 49/08; B29C 49/18
(52) U.S. Cl. ............... 264/523; 264/527; 264/532; 264/211.12; 264/178 T
(58) Field of Search ................. 264/523, 530, 264/209.1, 516, 527, 532, 211.12, 178 R

(56) References Cited

U.S. PATENT DOCUMENTS

| 4,154,244 A | 5/1979 | Becker et al. .......... 128/349 B |
| 4,254,774 A | 3/1981 | Boretos ................. 604/271 |
| 4,331,786 A | 5/1982 | Foy et al. ............... 525/408 |

(List continued on next page.)

FOREIGN PATENT DOCUMENTS

| EP | 274 411 A2 | 1/1988 |
| EP | 0 420 488 B1 | 4/1991 |
| EP | 0 485 903 B1 | 5/1992 |
| EP | 0 513 459 A1 | 11/1992 |
| EP | 0 540 858 A1 | 5/1993 |
| EP | 0592885 A2 | 9/1993 |
| EP | 0 566 755 A1 | 10/1993 |
| FR | 2 651 681 | 3/1991 |
| WO | 84/01513 | 4/1984 |
| WO | 92/08512 | 5/1992 |
| WO | 92/19316 | 11/1992 |
| WO | 95/23619 | 9/1995 |
| WO | 96/04951 | 2/1996 |
| WO | 97/326247 | 3/1996 |
| WO | 96/12516 | 5/1996 |

OTHER PUBLICATIONS

Flesher, "Polyether block amide, high–performance TPE," Modern Plastics, Sep. 1987 pp. 100, 105, 110.

Koch, "PEBAX (Polyether Block Amide)", Advances in Polymer Technology, vol. 2, No. 3 1982 pp. 160–162.

(List continued on next page.)

*Primary Examiner*—Michael Colaianni
*Assistant Examiner*—Monica A Fontaine
(74) *Attorney, Agent, or Firm*—Vidas, Arrett & Steinkraus PA

(57) ABSTRACT

A process for blowing a balloon from a tubular parison of a thermoplastic polymer material by radially expanding the parison at an elevated temperature and pressure, the process characterized in that:

a) the polymer material includes a "H-bonding" polymer which undergoes interchain hydrogen bonding between at least some segments thereof;

b) the parison is conditioned in a high moisture environment prior to blowing, and c) the balloon is blown after moisture conditioning of the parison and without an intervening drying thereof.

H-bonding polymers may be polyamides, polyurethanes or block copolymers containing a polyamide or polyurethane block. The process reduces occurrence of fish eye defects in the formed balloons.

17 Claims, 4 Drawing Sheets

U.S. PATENT DOCUMENTS

| | | | |
|---|---|---|---|
| 4,332,920 A | 6/1982 | Foy et al. | 525/408 |
| 4,385,635 A | 5/1983 | Ruiz | 600/435 |
| 4,413,989 A | 11/1983 | Schjeldahl et al. | 604/96 |
| 4,490,421 A | 12/1984 | Levy | 428/35 |
| 4,563,181 A | 1/1986 | Wijayarathna | 604/523 |
| 4,675,361 A | 6/1987 | Ward, Jr. | 525/92 A |
| 4,772,347 A * | 9/1988 | Fowler | 156/167 |
| 4,786,556 A | 11/1988 | Hu et al. | 428/412 |
| 4,886,506 A | 12/1989 | Lovgren et al. | 604/530 |
| 4,898,591 A | 2/1990 | Jang et al. | 604/282 |
| 4,906,244 A | 3/1990 | Pinchuk et al. | |
| 4,938,676 A | 7/1990 | Jackowski et al. | 425/140 |
| 4,950,239 A | 8/1990 | Gahara et al. | 604/96 |
| 4,950,257 A | 8/1990 | Hibbs et al. | 604/265 |
| 4,952,357 A | 8/1990 | Euteneuer | 264/129 |
| 4,971,667 A | 11/1990 | Yamazaki et al. | 204/192.32 |
| 5,250,069 A | 10/1993 | Nobuyoshi et al. | 606/192 |
| 5,270,086 A * | 12/1993 | Hamlin | 428/35.2 |
| 5,281,677 A | 1/1994 | Onwunaka et al. | 525/149 |
| 5,290,306 A | 3/1994 | Trotta et al. | 606/194 |
| 5,295,978 A | 3/1994 | Fan et al. | 604/265 |
| 5,300,048 A | 4/1994 | Drewes, Jr. et al. | 604/280 |
| 5,304,134 A | 4/1994 | Kraus et al. | 604/96 |
| 5,328,468 A | 7/1994 | Kaneko et al. | |
| 5,336,675 A | 8/1994 | Snorrason | 128/842 |
| 5,344,400 A | 9/1994 | Kaneko et al. | 604/96 |
| 5,348,538 A | 9/1994 | Wang et al. | |
| 5,397,306 A | 3/1995 | Nobuyoshi et al. | 604/96 |
| 5,478,320 A | 12/1995 | Trotta | 604/96 |
| 5,512,051 A | 4/1996 | Wang et al. | 604/96 |
| 5,556,383 A | 9/1996 | Wang et al. | |
| 5,714,110 A | 2/1998 | Wang et al. | |
| 5,716,561 A * | 2/1998 | Guergov | 264/40.1 |
| 6,461,326 B1 * | 10/2002 | Yang et al. | 604/96.01 |

OTHER PUBLICATIONS

De, et al. eds. *Thermoplastic Elastomer from Rubber–Plastic Bends, Chapter1*, Ellis Horwoal, New York pp. 13–27.

Gorski, The Nomenclature of Thermoplastic Elastomers, Kunstoffe German Plastics, 83 (1993) No. 3, pp. 29–30.

Hofmann, Thermoplastic Elastomers, Kunstoffe German Plastics, 80 (1990) No. 10, pp. 88–90.

Atochem, "Pebax ® Resins 33 Series Property Comparison" undated, (1 pg manufacturers technical information sheet received Sep. 29, 1994.

Atochem, undatd and untitled brochure for Pebex ® resins, pp. 2–5. Not available.

Bhowmick, et al. eds., *Handbook of Elastomers*, Chapters 10 and 12, Marcel Dekker Inc., pp. 341–373 and 411–442.

Walker, et al. eds. *Handbook of Thermoplastic Elastomers*, Chapter 8, Van Nostrand Reinhold Co., NY pp. 258–281.

U.S. application Ser. No. 09/672330, Nao Pao Lee et al., filed Sep. 2000.

* cited by examiner

WET PROCESSING METHOD FOR CATHETER BALLOONS

Balloons are widely used on medical devices, such as catheters, employed in various medical treatments. Examples of such treatments include repair of the vascular system, e.g. angioplasty, stent placement, and the like and in treatment and repair of disorders of the gastrointestinal, bronchial or esophageal tracts. Such balloons may be made of a wide variety of materials. With some of these materials, namely polyamides ("nylons"), polyurethanes and block copolymers comprising polyamide or polyurethane segments, hydrogen bonding between chains of the molecule plays a significant role in the strength profile of the formed balloon.

U.S. Pat. No. 4,906,244 issued in March 1990 to Pinchuk et al describes balloons of certain aliphatic polyamides and states that "nylon materials have been observed to exhibit desirable stability during processing to the extent that they do not absorb excessive moisture from the environment if the parison is allowed to stand uncovered for reasonable time periods."

U.S. Pat. No. 5,328,468 describes medical device balloons made of an aromatic polyamide.

U.S. Pat. No. 5,556,383 describes medical device balloons made of a block copolymer comprising polyamide segments.

EP 0592885 describes medical device balloons made of a thermoplastic polyurethane.

U.S. Pat. No. 5,714,110 describes an improved method of preparing an oriented balloon of thermoplastic material comprising extruding a hollow tube of the thermoplastic material and subsequently expanding the tube by subjecting the tubing, while in a mold, to an elevated temperature and an increased interior pressure to produce an oriented balloon, the invention being characterized in that the tube is subjected to a drying step, prior to the expanding step, thereby increasing the strength of the balloon relative to a reference balloon prepared in the same manner, except for said drying step.

Hence until now it has been considered that the moisture content of a parison of thermoplastic polymer material used to form a medical balloon was not a particular concern, or that if it was a concern, the parison should be dried before blowing the parison into a balloon.

In forming balloons by radial expansion of a tubular parison it is often necessary to use a very high blowing pressure to initiate radial expansion at conventional blowing temperatures of about 90° C. to about 110° C. Once initiated, however, the high pressure causes very rapid growth as the polymer material gets increasingly thinner, until the expanding polymer material reaches the mold wall. This rapid growth has been associated with a number of common defect problems, such as balloons displaying "fish eye" defects.

In copending U.S. application Ser. No. 09/672,330, filed Sep. 28, 2000, it is taught that a slower balloon growth rate can reduce fish eye defects, but the technique of obtaining a lowered growth rate in that application requires modification of parison configurations.

SUMMARY OF THE INVENTION

It has now surprisingly been discovered that significant benefits can be obtained in forming a balloon from a parison of a thermoplastic polymer which undergoes substantial intermolecular hydrogen bonding, when the parison is conditioned in a high humidity environment prior to blowing the balloon. Accordingly the invention in one aspect is a process for blowing a balloon from a tubular parison of a thermoplastic polymer by radially expanding the parison at an elevated temperature and pressure, the process characterized in that:

a) the polymer is one which undergoes hydrogen bonding between at least some segments thereof ("a H-bonding polymer");

b) the parison is conditioned in a high moisture environment prior to blowing, and c) the balloon is blown after moisture conditioning of the parison and without an intervening drying thereof.

Moisture conditioning is continued for a time sufficient to obtain a stable reproducible high moisture content, suitably about 8 hrs or more in an environment of at least 80% RH.

Further aspects of the invention will become apparent from the detailed description which follows.

DESCRIPTION OF PREFERRED EMBODIMENTS

Figure 1:
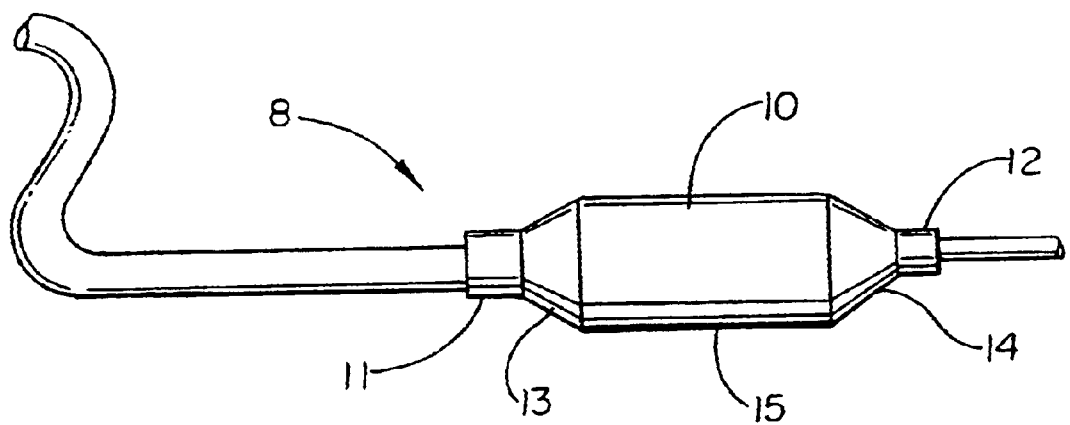
FIG. 1 is a fragmentary side view of a medical catheter having mounted thereon a balloon produced in accordance with the invention.

Referring to FIG. 1 there is shown therein a medical device catheter 8 having mounted thereon a balloon 10, suitable for mounting on a catheter. Balloon 10 comprises oppositely disposed waist portions 11, 12, cone portions 13, 14, and body portion 15. Balloon 10 is made from polymer material.

The polymers employed in the inventive process which have hydrogen bonding sites, particularly N—H groups along the length of the polymer chain or on groups pendant thereto. Polyamides, polyurethanes, and block copolymers containing polyamide or polyurethane segments are preferred examples of such polymers. Thermoformable graft or comb copolymers comprising polyurethane and/or polyamide segments may also be used.

Polyamides may be aliphatic or aromatic. Examples of aliphatic polyamides include nylon 6, nylon 6/6, nylon 6/10, nylon 6/12, nylon 9, nylon 11 and nylon 12, Examples of aromatic polyamides include polyamides prepared by polycondensing xylylenediamine with an aliphatic dicarboxylic acid such as adipic acid, and polyamides prepared by polycondensing isophthalic acid and an aliphatic diamine such as hexamethylenediamine. Nylon MXD6 and nylon 6I, manufactured by Mitsubishi Gas Chemical Company, Inc., are specific such polymers.

Polyurethanes may be any thermoplastic polyurethanes suitable for use in forming balloons including polyurethanes derived from polyester polyols or polyether polyols or mixtures thereof and aromatic or aliphatic polyisocyanates. Such polyurethanes may be elastomeric or engineering polymers. Specific examples of polyurethanes include Tecothane® aromatic polyurethane-polyether polymers, and polyurethane-polyethers and polyurethane-polyesters sold under the Pellethane® trademark by Dow, for instance and Pellethane® 2102, 2103, 2202, 2353, 2354, 2355 and 2363. Bionate® polycarbonate-urethane polymers from Polymer Technology Group, Inc., for instance Bionate®80A may also be used. Engineering polyurethanes may also be used, for instance Isoplast® polyurethanes, such as Isoplast® 301, sold by Dow and Tecoplast TP-470 Series resins sold by Thermedics, Inc.

Block copolymers include segmented polyamide-polyether-polyesters sold under the Pebax® trademark, in particular Pebax 6333, Pebax 7033 and Pebax 7233, and aliphatic polyurethane-polyether block copolymers, sold by Thermedics, Inc., under the Tecoflex® mark, for instance Tecoflex® 80A. Some of the polyurethanes listed in the previous paragraph may be block copolymers.

Polymer blends may also be used in some cases, typically comprising at least one member of the blend being a polymer from the group described above. Preferably, such a blend would be a compatible mixture of a thermoplastic elastomer resin and a thermoplastic engineering resin.

The balloon wall may be from a single layer of the polymer material which engages in interchain hydrogen bonding, or such polymer may be one layer of a laminate balloon composed of two or more layers of thermoplastic polymer.

For polymer materials which engage in interchain hydrogen bonding, the presence of moisture has been considered to weaken such interchain bonding, in some cases lowering tensile strength up to as much as 45%. This is generally undesirable in the final balloon. However, such tensile strength weakening facilitates processing, resulting in a substantial reduction in processing defects such as "fish eye" defects (also referred to as "football" defects. Furthermore, excess moisture can be removed from the formed balloon after blowing, typically by equilibrating at ambient moisture, to yield a balloon which has comparable burst strength to balloons prepared without the parison moisture treatment step of the invention. Typically the drying equilibration can be much more rapid than moisture equilibration of the parison because the much thinner balloon wall rapidly loses excess moisture in a drier atmosphere.

Figure 2:
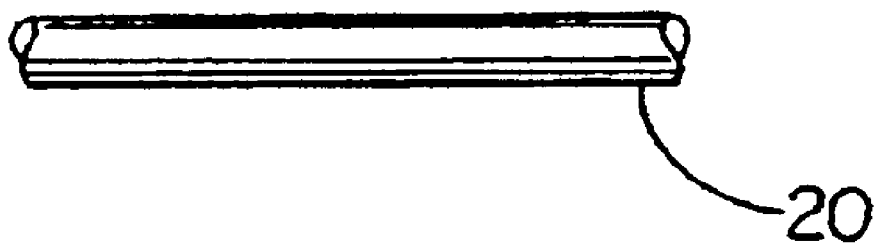
FIG. 2 is a fragmentary side view of an extruded tubular parison suitable for use in preparing a balloon in accordance with the invention.

Catheter balloons, such as depicted in FIG. 1, may be formed from tubular extrusions of the polymer material. Tubular extrusions may be prepared according to conventional procedures and segmented to form tubular parisons from which the medical device balloons will be formed. An extrusion of this type is depicted as 20 in FIG. 2.

The parisons may be formed of a single layer of polymer material or of multiple layers of the same or different polymers. Multilayer parisons may be formed by coextrusion or by other techniques known in the art.

For medical catheter balloons suited for dilatation or stent placement applications with nominal diameters of about 1.5–24 mm, extruded wall thicknesses (single wall basis) in the range of 0.003–0.036 inch (0.076–0.91 mm) and outer diameters in the range of 0.015–0.236 inch (0.38–6 mm) will typically be suitable.

After extrusion the parison is radially expanded into a medical catheter balloon.

In accordance with the present invention, after extrusion and before radial expansion the parison is conditioned in a moist environment, suitably a moist atmosphere. As used herein a moist atmosphere is considered to be at least 80% RH, ambient temp (18–23° C.), preferably at least 85% and more preferably at least 90% RH at ambient temp. If desired a higher temperature may be used with at least a corresponding mass quantity of moisture. Conditioning time is an amount sufficient to provide a stable reproducible high moisture content in the polymer. This will generally be for a time in excess of 1 hr which is sufficient to provide a moisture uptake rate in the parisons which is 10% or less, preferably 5% or less of the moisture content growth rate in the first hour of conditioning. Typical conditioning times will be from about 8 to about 48 hours. Preferably the time is sufficient to achieve substantial equilibration. Typically conditioning for a period of 24 hours or less at ambient temperature will be sufficient to achieve a state of substantial equilibration.

As an alternative to a moist atmosphere, the moist environment conditioning may be accomplished by soaking the parison in liquid water for a time sufficient to provide a stable reproducible moisture content in the polymer. Depending on the particular, liquid water soaking may require more or less time than moist atmosphere conditioning.

Accelerated conditioning at elevated temperature and/or pressure may be effective in some cases to shorten the conditioning time.

The moisture conditioning may be done on the parison as extruded, or on the parison after modification by performance of any desired intermediate stretching, ID expansion and/or cone/waist reduction steps, as known in the art. Alternatively, some or all of such intermediate stretching, ID expansion and/or cone/waist reduction steps may be performed after conditioning, promptly before blowing.

The moist parison is then blown into a balloon without drying the parison or allowing it to equilibrate at ambient RH. Any conventional blowing technique may be employed. Free blowing may be used, but typically parison will be expanded in a mold. Radial expansion is performed at a temperature above Tg but below melting temperature. For most suitable balloon materials the radial expansion will typically be in the range of about 85–140° C., although in some cases temperatures as high as about 200° C. may be feasible. For medical catheter balloons internal pressure of about 100 (689 kPa) to about 500 psi (3447 kPa) will generally be used to blow the balloon.

If desired, a heat setting step can be run at a temperature higher than the blow temperature (typically 5°–25° C. higher) but at a pressure lower than the blowing pressure (typically 20 psi (138 kPa) to about 100 psi (689 kPa). Heat setting can reduce balloon compliance and can increase the burst pressure of the balloon. Heat setting procedures which may be adapted for use in the inventive process are described in EP 274 411 A2 (C. R. Bard) and EP 592 885 A2 (C. R. Bard), both of which are incorporated herein by reference.

If it is desired to increase compliance or to provide a stepped compliance profile, the blown balloon, or a portion thereof may be shrunk by heating to a temperature somewhat below the blowing temperature (suitably to about 70° C.–80° C.) while pressurizing to at about 30 psi (207 kPa) to about 100 psi (689 kPa). Shrinking procedures which may be adapted for use in the inventive process are described in U.S. Pat. No. 5,348,538 (L. Wang, et al) and in WO 97/32624, both of which are incorporated herein by reference.

After the balloon has been blown and removed from the mold, excess moisture introduced by the parison moisture conditioning step of the invention can be easily removed, suitably by equilibration at ambient RH for a storage time of at least 8 hours, preferably one day or more.

The final product is a balloon as in FIG. 1.

Figure 3:
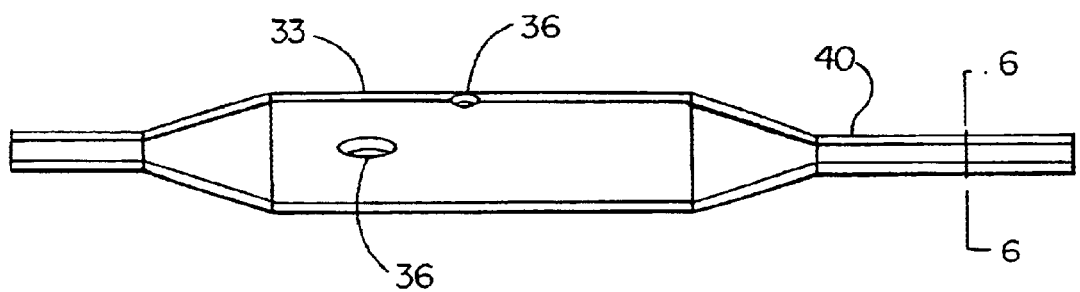
FIG. 3 is a schematic side view of a portion of a balloon produced in accordance with a prior art procedure and displaying a "fish-eye" defect.

As noted the process of the invention provides a lower level of defects commonly encountered in molded balloons. A lower material tensile strength is believed to produce a decrease in the strain rate sensitivity of an expanding parison. This in turn allows for a more uniform distribution of polymer material and produces a lower defect rate. In particular the number and size of "fish eye" or "football" defects is reduced. Balloon 33 in FIG. 3 includes a pair of fish eye defects 36 on the body portion thereof. Fish eye defects are believed to be due to regions in which polymer is relatively more gelled than the adjacent polymer material, or to the presence of localized microcontamination causing the defect region to be stressed more. The gelled or microcontaminated material, being less mobile, is not evenly redistributed if the balloon expansion occurs too quickly. With a reduced balloon growth rate the gelled material has time to redistribute itself more uniformly in the polymer mass.

Because the inventive process reduces the occurrence of such defects, a batch of about 50 or more, and preferably about 100 or more, sequentially produced balloons from a single production run is improved, relatively to a corresponding sequence of balloons produced without the moisture conditioning step. As such a sequential batch represents a distinctive and non-obvious manufacture, even though the individual non-defective members thereof may not be otherwise readily distinguishable.

Depending on the material and blowing techniques used yields of balloons free of fish-eye defects may be improved by 5–50% or more as a result of the use of a high moisture equilibrated parison in accordance with the invention.

In one experimental study, with controlled variations of 14 process variations using Pebax 7233 parisons, conditioning at approximately 90% RH, ambient temp, on average produced parison moisture contents in the range of 14,000–20,000 ppm, as determined by Karl Fisher titration. Ambient moisture content of the Pebax 7233 resin, per manufacturer's data, was approximately 7000 ppm. Yields of fish eye-free balloons made from parisons equilibrated at 90% RH before blowing were on average 10.3% higher than yields obtained from parisons stored at ambient RH of approximately 50%.

Figure 4:
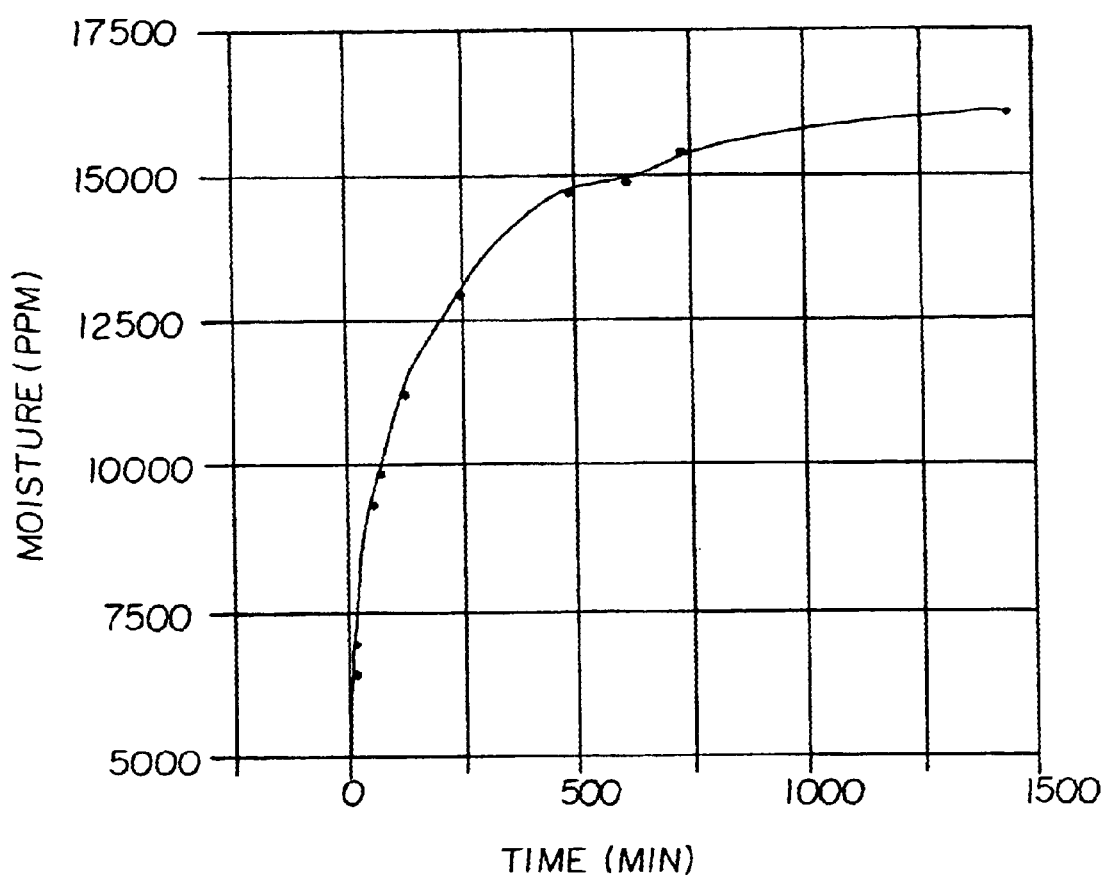
FIG. 4 is a graphical presentation of moisture uptake in parisons of Pebax® 7233 resin under conditions as specified below.

Referring to FIG. 4, there is shown a graph of Karl Fisher moisture titration data for a group of parisons stored at 72° F. (22° C.) at 92% RH, ambient pressure, for up to 24 hrs (1440 min). The moisture content initially increases rapidly from an initial content of about 7000 ppm to a content of 9900 ppm after 62 min, corresponding to an initial uptake in the first hour slightly in excess of 2800 ppm. The uptake rate continuously decreases, however, such that by 8 hours the growth rate in ppm/hr is less than 10% of the initial rate and the moisture content can be considered to be acceptably conditioned. By 24 hours the moisture content of about 16200 appears to be near an asymptotic limit indicating that the moisture content is substantially equilibrated.

Although the invention has been described especially in connection with polyamides and polyurethane, it will be recognized that other polymers which undergo interchain hydrogen bonding between at least some segments thereof may also be employed in the invention. For instance, polymers which form interchain links between H-donating groups such as —OH, —NH, and —SH groups on one molecule and receptor atoms on another molecule. Receptor atoms may be for instance oxygen atoms of carboxyl, ether, or hydroxyl groups, nitrogen atoms of an amine, amide, carbamate, cyano, isocyano, or other N-containing group, or fluoro atoms.

While the invention has been described in connection with what is presently considered to be the most practical and preferred embodiments, it is to be understood that the invention is not to be limited to the disclosed embodiments but, on the contrary, is intended to cover various modifications and equivalent arrangements included within the spirit and scope of the appended claims.

The above examples and disclosure are intended to be illustrative and not exhaustive. These examples and description will suggest many variations and alternatives to one of ordinary skill in this art. All these alternatives and variations are intended to be included within the scope of the claims, where the term "comprising" means "including, but not limited to". Those familiar with the art may recognize other equivalents to the specific embodiments described herein which equivalents are also intended to be encompassed by the claims. Further, the particular features presented in the dependent claims can be combined with each other in other manners within the scope of the invention such that the invention should be recognized as also specifically directed to other embodiments having any other possible combination of the features of the dependent claims. For instance, for purposes of claim publication, any dependent claim which follows should be taken as alternatively written in a multiple dependent form from all prior claims which possess all antecedents referenced in such dependent claim if such multiple dependent format is an accepted format within the jurisdiction (e.g. each claim depending directly from claim 1 should be alternatively taken as depending from all previous claims). In jurisdictions where multiple dependent claim formats are restricted, the following dependent claims should each be also taken as alternatively written in each singly dependent claim format which creates a dependency from a prior antecedent-possessing claim other than the specific claim listed in such dependent claim below.

The entire contents of all documents and copending applications mentioned anywhere in the present application are incorporated herein by reference.

What is claimed is:

1. A process for blowing a balloon from a tubule parison of a thermoplastic polymer material by radially expanding the parison at an elevated temperature and pressure, the process characterized in that:
   a) the polymer material comprises a H-bonding polymer, the H-bonding polymer being a polymer which undergoes interchain hydrogen bonding between at least some segments thereof;
   b) the prison is conditioned in a high moisture environment prior to blowing, wherein the high moisture environment is a high humidity atmosphere of at least 80% relative humidity at ambient temperature, and
   c) the balloon is blown after moisture conditioning of the parison and without an intervening drying thereof.

2. A process as in claim 1 wherein the balloon so formed is subsequently equilibrated at ambient relative humidity.

3. A process as in claim 1 wherein the high humidity atmosphere is at least 85% relative humidity at ambient temperature.

4. A process as in claim 3 wherein the high humidity atmosphere is at least 90% relative humidity at ambient temperature.

5. A process as in claim 1 wherein said H-bonding polymer is a polymer having N-H groups along at least a portion of the length of the polymer chain or on groups pendant thereto.

6. A process as in claim 1 wherein said H-bonding polymer is selected from the group consisting of polyamides, polyurethanes, and block copolymers containing polyamide or polyurethane segments.

7. A process as in claim 6 wherein said H-bonding polymer is a polyamide.

8. A process as in claim 7 wherein said polyamide is selected from the group consisting of nylon 6, nylon 6/6, nylon 6/10, nylon 6/12, nylon 9, nylon 11, nylon 12, polyamides prepared bypolycondensing xylylenediamine with an aliphatic dicarboxylic acid, and polyamides prepared by polycondensing isophthalic acid and an aliphatic diamine.

9. A process as in claim 6 wherein said H-bonding polymer is a polyurethane.

10. A process as in claim 6 wherein said H-bonding polymer is a block copolymer containing polyamide or polyurethane segments.

11. A process as in claim 10 the block copolymer is a polyamide-polyether-polyester.

12. A process as in claim 1 wherein the thermoplastic polymer material is a polymer blend comprising at least one said H-bonding polymer.

13. A process as in claim 1 wherein the parison is a multi-layer laminate at least one layer of which is composed of said H-bonding polymer.

14. A process as in claim 1 wherein the parison is conditioned for a time in excess of one hour which is sufficient to produce a moisture content growth rate which is 10% or less of the moisture content growth rate growth rate in the first hour of conditioning.

15. A process in claim 14 wherein said conditioning time is sufficient to produce a moisture content growth rate which is 5% or less of the moisture content growth rate growth rate in the first hour of conditioning.

16. A process as in claim 15 wherein the conditioning time is sufficient to produce a substantially equilibrated moisture content.

17. A process as in claim 1 wherein the parison is conditioned in said high moisture environment by soaking in liquid water.

* * * * *